United States Patent [19]
Lewis et al.

[11] Patent Number: 6,090,965
[45] Date of Patent: Jul. 18, 2000

[54] REMOVAL OF DISSOLVED SILICATES FROM ALCOHOL-SILICON DIRECT SYNTHESIS SOLVENTS

[75] Inventors: Kenrick Martin Lewis, Rego Park; Hua Yu, White Plains; Regina N. Eng, Syossett, all of N.Y.

[73] Assignee: OSi Specialties, Inc., Greenwich, Conn.

[21] Appl. No.: 09/054,027

[22] Filed: Apr. 2, 1998

[51] Int. Cl.$^7$ .................. C07F 7/18; C07F 7/04
[52] U.S. Cl. ............... 556/470; 568/635; 585/24; 585/25; 585/26
[58] Field of Search ............... 552/470; 568/635; 585/25, 24, 26

[56] References Cited

U.S. PATENT DOCUMENTS

| | | | |
|---|---|---|---|
| 2,486,992 | 11/1949 | Sowa | 260/448.2 |
| 2,692,838 | 10/1954 | Thurber | 117/102 |
| 3,627,807 | 12/1971 | Bieh | 260/448.8 |
| 3,641,077 | 2/1972 | Rochow | 260/429 |
| 3,775,457 | 11/1973 | Muraoka et al. | 260/448.8 |
| 3,803,197 | 4/1974 | Anderson et al. | 260/448.8 |
| 4,113,761 | 9/1978 | Kreuzburg et al. | 260/448.8 |
| 4,288,604 | 9/1981 | Magee et al. | 556/470 |
| 4,323,690 | 4/1982 | Montle et al. | 556/470 |
| 4,727,173 | 2/1988 | Mendicino | 556/470 |
| 4,752,647 | 6/1988 | Inaba et al. | 556/470 |
| 4,761,492 | 8/1988 | Childress et al. | 556/482 |
| 4,762,939 | 8/1988 | Mendicino | 556/470 |
| 4,778,910 | 10/1988 | Stoffer et al. | 556/470 |
| 4,950,779 | 8/1990 | Wengrovius et al. | 556/457 |
| 4,999,446 | 3/1991 | Moody et al. | 556/470 |
| 5,084,590 | 1/1992 | Ritscher et al. | 556/470 |
| 5,103,034 | 4/1992 | Cho et al. | 556/470 |
| 5,166,384 | 11/1992 | Bailey et al. | 556/466 |
| 5,260,471 | 11/1993 | Yamada et al. | 556/470 |
| 5,362,897 | 11/1994 | Harada et al. | 556/470 |
| 5,378,790 | 1/1995 | Michalczyk et al. | 528/35 |
| 5,412,016 | 5/1995 | Sharp | 524/430 |
| 5,441,718 | 8/1995 | Sharp | 423/338 |
| 5,527,937 | 6/1996 | Standke et al. | 556/470 |
| 5,728,858 | 3/1998 | Lewis et al. | 556/470 |

OTHER PUBLICATIONS

"Polydiethylsiloxane Liquids" by N.S. Leznov, L. A. Sabun and K. A. Andrianov, Russ. *J. Gen Chem.* 29 (1959), 1508–1513 (Russian pagination), pp. 1482–1487.

"Polydiethylsiloxane Liquids" by N.S. Leznov, L. A. Sabun and K. A. Andrianov, Russ. *J. Gen Chem.* 29 (1959), 1508–1513 (Russian pagination), pp. 1492–1495.

"Various Factors Affecting The Conversion of Silicon Alkoxide Solutions To Gels", by Sumio Sakka, in *Ultrastructure Processing of Advanced Ceramics*, edited by John D. Mackenzie, pp. 159–171.

"Populations Of Oligomers in Sol–Gel Condensation" by F. Brunet and B. Cabane, *J.Phys. Chem.* 1991, 95, 945–951, pp. 211–225.

"Sol–Gel Polymerization Studied Through SI NMR With Polarization Transfer", by F. Brunet et al, 1991 *The Journal of Physical Chemistry*, vol. 95, No. 2, 1991, pp. 945–951.

*Primary Examiner*—Paul F. Shaver
*Attorney, Agent, or Firm*—Edward K. Welch, II; Andrew S. Reiskind; Timothy X. Witkowski

[57] ABSTRACT

Dissolved silanes, silicones and silicates from solvents used in the slurry phase Direct Synthesis of alkoxysilanes are removed by adding a carboxylic acid such as formic acid to generate filterable precipitates and reusable solvent. The solvents are thereby remediated and made suitable for reuse in Direct Synthesis processes. Foaming is reduced with the remediated solvent and silicon conversion rates are higher. The precipitates are easily filtered and retain negligible quantities of solvent.

24 Claims, No Drawings

REMOVAL OF DISSOLVED SILICATES FROM ALCOHOL-SILICON DIRECT SYNTHESIS SOLVENTS

FIELD OF THE INVENTION

The present process relates to the removal of dissolved silanes, silicones and silicates from solvents used in the slurry phase Direct Synthesis of alkoxysilanes. The solvents are remediated thereby and made suitable for reuse in said Direct Synthesis. More particularly, the present invention discloses the use of carboxylic acids, preferably formic acid, to react with the dissolved silanes, silicones and silicates to generate readily filterable precipitates and reusable solvent.

BACKGROUND OF THE INVENTION

Trialkoxysilanes, especially trimethoxysilane and triethoxysilane, are used in the production of silane coupling agents. One method of synthesis of trialkoxysilanes is directly from silicon and an alcohol. This method is known variously in the art as the Direct Synthesis, the Direct Reaction, the Direct Process or the Rochow Reaction.

For trialkoxysilanes, Direct Synthesis is most conveniently performed in slurry reactors. In a slurry reactor for the Direct Synthesis of trialkoxysilanes, catalytically-activated silicon particles are maintained in suspension in an inert, high boiling solvent and are made to react with an alcohol at an elevated temperature. This type of reaction is disclosed in U.S. Pat. Nos. 3,641,077; 3,775,457; 4,727,173; 4,761,492; 4,762,939; 4,999,446, 5,084,590; 5,103,034; 5,362,897; 5,527,938, in co-pending U.S. application Ser. No. 08/728,228 filed Oct. 10, 1996, now U.S. Pat. No. 5,728,858 and application Ser. No. 08/729,266 filed Oct. 10, 1996, now U.S. Pat. No. 5,783,720 and in Japanese Kokai Tokkyo Koho 55-28928 (1980), 55-28929 (1980), 55-76891 (1980), 57-108094 (1982) and 62-96433 (1987), 06-306083 (1994), all of which are incorporated herein by reference. Solvents disclosed in the aforementioned patents do not degrade under the activation and reaction conditions. Preferred examples are organic solvents with normal boiling points higher than about 250° C. that are stable at high temperature, and that are typically used as heat exchange media. Solvents meeting these criteria include the commercial products THERMINOL®59, THERMINOL®60, THERMINOL®66, DOWTHERM®HT, MARLOTHERM®S, MARLOTHERM®L, as well as diphenyl ether, diphenyl, terphenyl, alkylated benzenes, alkylated diphenyls and alkylated terphenyls.

Tetraalkoxysilanes (also called alkyl silicates, esters of orthosilicic acid and silicon alkoxides) are prepared in slurry-phase Direct Synthesis processes wherein the solvent is often the product itself. The catalyst can be copper or a copper compound, but is usually an alkali or alkali metal salt of a high boiling alcohol. Such processes are disclosed in U.S. Pat. Nos. 3,627,807; 3,803,197; 4,113,761; 4,288,604 and 4,323,690, all incorporated herein by reference. Ethyl silicate is the tetraalkoxysilane manufactured in greatest amounts. It and its partially hydrolyzed derivatives are used for coatings, especially corrosion resistant zinc-rich coatings, and as bonding agents for a wide variety of molding and precision casting applications.

During the course of the Direct Synthesis of trialkoxysilanes, byproducts such as alkyl silicates accumulate in the solvent and contribute to an increase in viscosity, to a decline in catalytic activity and to foaming in the reaction slurry. These effects limit the long-term use of the solvent and necessitate its disposal or remediation. R. J. Ayen et al., "Better Ceramics Through Chemistry II," C. J. Brinker, D. E. Clark and D. R. Ulrich, Editors, Materials Research Society, Pittsburgh, Pa., 1986. pp 801–808, acknowledge this problem occurs with tetraethoxysilane manufacture, but they disclose no specific method of solvent or slurry disposal or recovery. U.S. Pat. No. 5,166,384 discloses the use of borates and alkali metal akoxides to precipitate the contaminants and render the solvent reusable.

Leznov, et al. in *Journal of General Chemistry, USSR,* 29 (1959) 1482–1487 describe an acidolysis reaction of Si—OR (R=aliphatic or aromatic group) and SiOH functional groups using carboxylic acids such as formic and acetic acids for the synthesis of cyclic and linear poly (diethylsiloxanes). Similar acidolysis reactions have also been employed in U.S. Pat. No. 2,486,992 to prepare water repellant textile finishes; in U.S. Pat. No. 2,692,838 to Produce colloidal silica suitable for coating; in U.S. Pat. No. 4,950,779 for polysiloxane synthesis; in U.S. Pat. Nos. 5,378,790; 5,412,016; 5,441,718 and in S. Sakka, et al., "Ultrastructure Processing of Advanced Ceramics," (J. D. Mackenzie and D. R. Ulrich, Editors, John Wiley & Sons, N.Y. 1988, pp 159–171) for the preparation of silicate gels. None of these references suggests a use of carboxylic acids to remove dissolved silicates and other contaminants so as to remediate used Direct Synthesis reaction solvent prior to its reuse.

SUMMARY OF THE INVENTION

The present invention provides a method for the remediation and reuse of solvents from the Direct Synthesis of trialkoxysilanes and tetraalkoxysilanes. The method comprises the use of carboxylic acids in an acidolysis reaction to yield a solid product from the dissolved silicates, siloxanes and silanes in the contaminated solvent. Thereafter, the remediated solvent is recovered for reuse in the Direct Synthesis process. Recovery may be accomplished by separation of the solvent from the solids material, and, if necessary, removal of excess acid from the separated solvent.

Filtration aids are optionally used prior to or after the carboxylic acid treatment to facilitate liquid/solid separation and improve the overall efficiency of the solvent remediation process.

The overall process in less wasteful of raw materials, more commercially viable and more environmentally acceptable than current commercial processes.

DETAILED DESCRIPTION OF THE INVENTION

Slurry-phase reactors for the Direct Synthesis of alkoxysilanes and tetraalkoxysilanes may be operated in a batchwise or continuous mode. In batchwise operation, a single addition of silicon and catalyst is made to the reactor at the outset and alcohol is added continuously, or intermittently, until the silicon is fully reacted, or reacted to a desired degree of conversion. The alcohol typically is added in the gas phase but liquid phase addition is also feasible. In continuous operation, silicon and catalyst are added to the reactor initially and thereafter to maintain the solids content of the slurry within desired limits. The batchwise mode is illustrated in U.S. Pat. No. 4,727,173 and in the copending application Ser. No. 08/728,228 (filed Oct. 10, 1996) and application Ser. No. 08/729,266 (filed Oct. 10, 1996) for the Direct Synthesis of trialkoxysilanes, all incorporated herein by reference. The desired reaction products are removed from the reactor in a gas phase mixture with alcohol reactant. Isolation of the product is accomplished readily by distillation according to known procedures.

Continuous Direct Synthesis of trialkoxysilanes is disclosed in U.S. Pat. No. 5,084,590 and of tetraalkoxysilanes in U.S. Pat. Nos. 3,627,807; 3,803,197 and 4,752,647, all incorporated herein by reference.

Silicon metal, catalyst and solvent can be added together in the reactor in any order. The solvent is present in an amount sufficient to disperse the solid and gaseous reactants homogeneously. Generally, reactions are initiated with solvent and solids in a gravimetric ratio between 1:2 and 4:1, preferably 1:1 to 2:1. However, as the silicon is consumed during batchwise Direct Synthesis, the solvent to solids ratio will increase. The ratio can be maintained within narrow limits of the preferred range for continuous reactions.

The desired reaction products are removed from the reactor in a gas phase mixture with alcohol reactant. Selection for trialkoxysilane or tetraalkoxysilane can be accomplished by appropriate choice of catalyst and reaction conditions. Isolation of the desired trialkoxysilane and/or tetraalkoxysilane from alcohol reactant is readily accomplished by distillation according to known procedures.

Owing to the disadvantages (for example, foaming, viscosity increases and loss of reaction efficiency) brought about by the accumulation of dissolvent silicates and unreacted solids, the solvent must occasionally be treated for removal of these wastes. Otherwise, the performance of the Direct Synthesis deteriorates and the process becomes uneconomic.

The following equations are representations of the principal chemical reactions occurring during the Direct Synthesis of trialkoxysilanes and tetraalkoxysilanes.

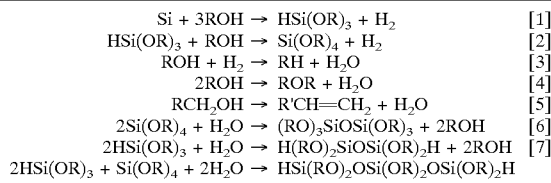

$$Si + 3ROH \rightarrow HSi(OR)_3 + H_2 \quad [1]$$
$$HSi(OR)_3 + ROH \rightarrow Si(OR)_4 + H_2 \quad [2]$$
$$ROH + H_2 \rightarrow RH + H_2O \quad [3]$$
$$2ROH \rightarrow ROR + H_2O \quad [4]$$
$$RCH_2OH \rightarrow R'CH=CH_2 + H_2O \quad [5]$$
$$2Si(OR)_4 + H_2O \rightarrow (RO)_3SiOSi(OR)_3 + 2ROH \quad [6]$$
$$2HSi(OR)_3 + H_2O \rightarrow H(RO)_2SiOSi(OR)_2H + 2ROH \quad [7]$$
$$2HSi(OR)_3 + Si(OR)_4 + 2H_2O \rightarrow HSi(RO)_2OSi(OR)_2OSi(OR)_2H$$

Desirable products of the Direct Synthesis of trialkoxysilanes have the general formula, $HSi(OR)_3$, wherein R is an alkyl group of 1 to 6 carbon atoms. R is preferably methyl and ethyl. Byproducts of the synthesis comprise $Si(OR)_4$, $RSiH(OR)_2$, $RSi(OR)_3$, linear, branched and cyclic silicates such as $(RO)_3SiOSi(OR)_3$, $H(RO)_2SiOSi(OR)_2H$, $HSi(RO)_2OSi(OR)_3$, $(RO)_3SiOSi(OR)_2R$, $(RO)_3SiOSi(RO)_2OSi(RO)_3$, $(RO)_3SiOSi(OR)HOSi(OR)_3$, $(RO)_3SiOSi(OR)ROSi(OR)_3$, $(RO)Si[OSi(OR)_3]_3$, $(RO)_3SiOSi(OR)(OSi(OR)_3)OSi(OR)_3$, and $[OSi(OR)_2]_n$, (n=4, 5, 6 . . . ), hydrogen gas, hydrocarbons (RH) such as methane and ethane, alkenes ($R'CH=CH_2$) such as ethylene and ethers (ROR) such as dimethyl ether and diethyl ether. In the general formula, $R'CH=CH_2$, for the alkene byproducts, R' is hydrogen or an alkyl group of 1 to 4 carbon atoms. Hydrogen gas, hydrocarbons and the ethers typically are not condensed in the cold trap with the liquid products and exit the apparatus as a gaseous stream. Some of the silicates are volatilized out of the reactor and are soluble in the liquid reaction product. Most remain solubilized in the solvent or precipitate as insoluble gels.

The Direct Synthesis of tetraalkoxysilanes is represented by equation [9].

$$Si + 4ROH \rightarrow Si(OR)_4 + 2H_2 \quad [9]$$

Similar silicate and gaseous byproducts are formed as in the trialkoxysilane Direct Synthesis.

Descriptions of the silicon and copper raw materials used in the Direct Synthesis of trialkoxysilanes are provided in U.S. Pat. Nos. 3,775,457 and 4,727,173, and in the copending application Ser No. 08/728,228, filed Oct. 10, 1996 now U.S. Pat. No. 5,728,858 and application Ser. No. 08/729,266, filed Oct. 10, 1996, now U.S. Pat. No. 5,783,720, all incorporated herein by reference. Used solvent also contains dark colored particles, which are derived from the silicon and copper or alkali metal catalyst charged to the reactor. The particles may contain silicon, copper, iron, aluminum, chromium, manganese, nickel, oxygen, phosphorus and titanium among other elements, and sometimes are difficult to separate by filtration or centrifugation, especially if gelatinous silicates are also present. Primary particles range in size from submicrometer to about 50 micrometers. Agglomerates are considerably larger.

Solid and/or liquid filtration aids optionally are added to facilitate separation of these solids prior to or subsequent to the addition of the carboxylic acid. Suitable filtration aids include cellulose-based products such as SOLKAFLOC®; acrylates such as GOOD-RITE®7058, CARBOPOL®980, PEMULEN®TR1, PEMULEN®TR2, and PEMULEN®1622; MILLITHIX®925; polyethylene oxide, polypropylene oxide and their copolymers; diatomaceous filter aids such as CELITE® and CELATOM® products; and inorganic silicates like calcium silicate and magnesium silicate. Mixtures of these filter aids may also be employed advantageously. The quantity of filter aid required for effective solids collection depends, among other factors, on the particle size and surface properties of the filter aid, on the solids content of the used reaction solvent and whether they are gelatinous or crystalline. As little as 0.1 weight percent (based on total weight of used solvent) might be sufficient in some cases, whereas in others an amount of filter aid equal to the weight of the contained solids might be necessary for fast, uninterrupted filtration and clarification. In cases where the solids are primarily gelatinous, still higher amounts of filter aid may be necessary. Additionally, it is often found experimentally that some materials exhibit an optimum use level beyond which the excess filtration aid might slow the rate of filtration. Thus, all cellulosic, siliceous, acrylate and polymeric filter aids are not all equally effective. Preferred materials for the process of this invention are SOLKAFLOC®, PEMULEN®TR1, PEMULEN®TR2, PEMULEN®1622, GOOD-RITE®7058 and CARBOPOL®980.

It is preferable to remove the suspended solids prior to the acidolysis to minimize the consumption of acid in the formation of metal carboxylates. However, it will be illustrated by example that this step is not absolutely required. Separation of solids from the used solvent with the aid of effective amounts of filter aid is desirable if the solvent is recycled to the Direct Synthesis without precipitation of dissolved silicates.

Slurry for disposal from the Direct Synthesis of tetraalkoxysilanes is similar to that just described, but has considerably less copper and more alkali metal salts (for example, potassium formate, sodium ethoxide, sodium methoxide or sodium 2-ethoxyethylate). These salts make the slurry very alkaline and increase the quantity of carboxylic acid required for precipitation of the dissolved silicates.

Solvents useful in the Direct Synthesis of alkoxysilanes are thermally stable and do not degrade under the activation and reaction conditions of the synthesis. The preferred solvents for trialkoxysilanes are high temperature stable organic solvents typically used as heat exchange media. Examples include THERMINOL®59, THERMINOL®60, THERMINOL®66, DOWTHERM®HT, MARLOTHERM®S, MARLOTHERM®L, diphenyl ether, diphenyl, terphenyl and alkylated benzenes, alkylated diphenyls and alkylated terphenyls with normal boiling points higher than about 250° C.

THERMINOL® is the Monsanto Company trade name for heat transfer fluids. THERMINOL®59 is a mixture of alkyl-substituted aromatic compounds recommended for use between −45 to 315° C. THERMINOL®60 is a mixture of polyaromatic compounds with an average molecular weight of 250. Its optimum temperature range is from −45° to 315° C. THERMINOL®66 and DOWTHERM®HT are mixtures of hydrogenated terphenyls with an average molecular weight of 240. Maximum temperature limit is about 370° C. THERMINOL®59, THERMINOL®66 and DOWTHERM®HT are preferred solvents of this invention. DOWTHERM®fluids are produced by Dow Chemical Company.

MARLOTHERM® is the Hüls AG trade name for its heat transfer fluids. MARLOTHERM®S is a mixture of isomeric dibenzylbenzenes. MARLOTHERM®L is a mixture of isomeric benzyl toluenes. Both can be used at temperatures up to about 350° C. Both are preferred solvents for the instant invention.

Suitable alkylated benzenes are dodecylbenzene, tridecylbenzene, tetradecylbenzene and their mixtures such as are sold by Vista Chemical Company under the trade name NALKYLENE®, NALKYLENE®550BL, NALKYLENE®550L and NALKYLENE®600L are particularly preferred solvents of this invention. Mixtures of alkylated benzenes and polyaromatic hydrocarbons are also useful solvents for the Direct Synthesis of alkoxysilanes.

The Direct Synthesis of tetraalkoxysilanes preferably is conducted with the product as solvent. However, aromatic solvents such as dibenzyltoluenes and diisopropylbenzene, and/or ether solvents such as triethyleneglycol dimethyl ether may be admixed with the trtraalkoxysilane. Useful solvents are identified in U.S. Pat. Nos. 3,803,197; 4,113,761 and 4,752,647, applicable portions of which are incorporated herein by reference.

Gravimetry and atomic absorption spectroscopy are suitable methods for quantifying the total silicon content of the used reaction solvent. Analytical procedures are published, for example, in "The Analytical Chemistry of Silicones," (A. L. Smith, Editor), John Wiley & Sons Inc., N.Y., 1991, chapter 8. Soluble silicates can be analyzed qualitatively and quantitatively by infra red spectroscopy. Si—O—Si bonds are indicated by strong absorption in the 1000–1200 $cm^{-1}$ range. $^{29}Si$ nuclear magnetic resonance (NMR) spectroscopy can be used to detect and quantify the different silicon-containing species in the used solvent.

In the nomenclature of silicon chemistry, silicon atoms bonded to four oxygen atoms are designated Q groups. $Q^0$ represents the monomers, $Si(OR)_4$. $Q^1$ designates the groups $OSi(OR)_3$, at the ends of chains. $Q^2$ denotes internal groups $OSi(OR)_2O$, in chains or cyclics. $Q^3$ refers to branching sites, $OSiO(OR)O$, and $Q^4$ to fully crosslinked groups, $Si(OSi)_4$. These groups have characteristic $^{29}Si$ NMR chemical shifts within the range, −70 to −120 ppm whose assignments are facilitated by the use of DEPT and depth pulse analysis. Publications by Brunet, et al. (*Journal of Physical Chemistry,* vol. 95 (1991), pp 945–951; and *Journal of Non-Crystalline Solids,* vol. 163 (1993) pp 211–225) and of Bendall, et al. (*Journal of Magnetic Resonance,* vol. 53 (1983) 365–385) detail the use of these NMR analytical techniques. The application of IR and NMR techniques to used hydrocarbon solvents from the Direct Synthesis of alkoxysilanes is illustrated hereinbelow in the Examples. Gas chromatographic (GC) analysis and mass spectrometry (MS) have also been found to be reliable and accurate techniques to quantify silicates in the used reaction solvent.

The instant method of waste treatment and reuse of solvent is applicable to any solvent or mixture of solvents employed in the Direct Synthesis of alkoxysilanes and tetraalkoxysilanes. The method comprises addition of a carboxylic acid to the used solvent, separation of the solid and volatile reaction products and recovery of the remediated solvent for reuse. In order to facilitate safe disposal of the solid waste, it is desirable to produce a granular solid, which settles or filters readily and which has little or no capacity to retain the reaction solvent.

Suitable carboxylic acids may have one or more COOH functional groups. Examples include the monocarboxylic acids, formic, acetic, furoic, acetoacetic, chloroacetic, chloropropanoic, trichloracetic, bromoacetic, fluoroacetic, trifluoroacetic, bromobenzoic, chlorobenzoic, lactic, glycolic and salicylic, the dicarboxylic acids, oxalic, maleic, fumaric, itaconic, succinic and adipic and polycarboxylic acids such as citric, tartaric and polyacrylic. Liquid, low molecular weight acids such as formic and acetic acids are preferred. These acids preferably are used as concentrated aqueous solutions available commercially. However, they may be diluted further with water prior to use provided such dilution does not impair the effectiveness of the solvent remediation and reuse. Thus, 80–99 weight percent formic and acetic acid reagents may be used effectively.

As is evident from equations [6, 7, 8] hereinabove, alkoxysilanes can react with water to produce condensed silicates. Further condensation of the reaction products shown in these equations can lead to gels and solids. Experiments with used Direct Synthesis solvents have shown that the contaminated solvents are water reactive, even with atmospheric moisture. Solids produced by the intentional addition of water to the used solvents are gelatinous and very difficult to separate from the solvents. They remain suspended or settle very slowly. Separation is improved with the use of filter aids, but the filter cake is sticky and solvent retentive. Addition of a carboxylic acid such as formic acid to the reaction mixture of used solvent and water, however, increases the settling rate of the solids and improves their separation. It is believed that the acid addition changes the solids by acidolysis of their silanol groups and/or alkoxy groups. Accordingly, the carboxylic acid solutions used in the process of the invention may be even more dilute then the reagent grade concentrations just mentioned. Aqueous solutions containing as low as 10 weight percent carboxylic acid may be effective in some instances. Preferably, the acid solution contains at least 25% carboxylic acid, more preferably at least 80 weight %.

Equations [10–16] illustrate the principal chemical reactions occurring in the used solvent when formic acid is the reagent acid. The SiOR and SiOH functionalities are present in dissolved or suspended silicates, silanes and siloxanes in the used solvent. SiOSi formation eventually leads to precipitation of solid silicates and silica. Alkyl formate and the corresponding alcohol are the volatile byproducts. They can be incinerated or used beneficially, if desired. For example, the ester-alcohol mixture can be used to wash excess acid and solvent from the precipitate solid prior to landfilling.

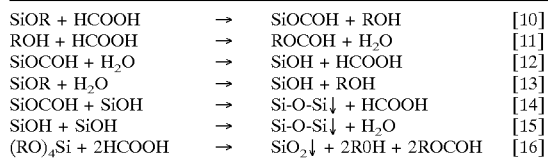

| SiOR + HCOOH | → | SiOCOH + ROH | [10] |
| ROH + HCOOH | → | ROCOH + H$_2$O | [11] |
| SiOCOH + H$_2$O | → | SiOH + HCOOH | [12] |
| SiOR + H$_2$O | → | SiOH + ROH | [13] |
| SiOCOH + SiOH | → | Si-O-Si↓ + HCOOH | [14] |
| SiOH + SiOH | → | Si-O-Si↓ + H$_2$O | [15] |
| (RO)$_4$Si + 2HCOOH | → | SiO$_2$↓ + 2R0H + 2ROCOH | [16] |

The quantity of carboxylic acid added to the waste solvent must be sufficient to precipitate the dissolved silicates and yield a reusable solvent. A deficiency of acid will be ineffective and an excess, besides being wasteful, can possibly result in undesirable Direct Synthesis performance when the solvent is reused. The optimum quantity can be estimated by analyzing the dissolved silicon content of the used solvent and utilizing an equivalents ratio of acid groups to silicon (that is, COOH/Si) in the range 0.5–6, or even higher. A preferred range is 1–3. When the slurry is alkaline, additional carboxylic acid usage will be required.

In the event that an excess of carboxylic acid is used, it can be removed from the treated solvent by evaporation, by adsorption on a suitable solid such as activated carbon or by chemical conversion to a volatile ester or insoluble salt. Evaporation can be effected at normal or reduced pressures, and with the aid of heat and an inert gas flow. For example, formic and acetic acids can be stripped from THERMI-NOL®59 at 50–100° C. and at atmospheric or lower pressures.

In a preferred embodiment, solvents used in the Direct Synthesis of trimethoxysilane or triethoxysilane are treated with a trialkylorthoester scavenger, (for example, the orthoformates, HC(OCH$_3$)$_3$ and HC(OC$_2$H$_5$)$_3$, the orthoacetates, CH$_3$C(OC$_2$H$_5$)$_3$ and CH$_3$C(OC$_3$H$_7$)$_2$OC$_2$H$_5$ and orthocarbonates (for example, C(OCH$_3$)$_4$, C(OC$_2$H$_5$)$_4$ and C(OC$_3$H$_7$)$_4$ to remove traces of carboxylic acids (for example formic and acetic) and/or other active hydrogen compounds from the filtrate recovered following precipitation of the dissolved silicates, siloxanes and silanes with said carboxylic acids.

The acids are converted to volatile esters via reactions such as that illustrated in equation [17].

| HCOOH + HC(OCH$_3$)$_3$ | → | 2HCOOCH$_3$ + CH$_3$OH | [17] |

Temperatures in the range, 15–250° C., preferably 20–100° C., may be used for safe and effective treatment of the used solvent. Selection of the most suitable temperature is determined by, among other factors, volatility of the ester and alcohol, exothermicity of the acidolysis, ease of filtration of the solids formed and configuration of the available equipment. The time of the acidolysis reaction can be from about ten minutes to about six hours or longer. Reaction times from about thirty minutes to about three hours are preferred for the process of the instant invention.

A process for the removal of dissolved silicates, silanes and siloxanes from the used solvents with carboxylic acids can be accomplished in a number of ways. In some cases, it might be advantageous to perform the acid treatment, prior to separation of the silicon and catalyst solids, in the same reactor used for the Direct Synthesis. Thus, after one or more batches of silicon has been reacted with an alcohol and there is a need to remediate and recycle the solvent, the alcohol feed to the reactor is terminated and the carboxylic acid is added to the stirred reaction slurry at a temperature that is above the normal boiling points of the ester and alcohol produced by equations [10, 11, 13]. These volatile byproducts (esters and alcohols) are taken overhead and optionally incinerated. Carboxylic acid is added at a rate and in an amount sufficient to remove the dissolved silicates, siloxanes and silanes. The slurry comprising silicon, catalyst (that is, containing copper, alkali metal or alkaline earth metal) solids, the precipitated silicates and solvent with minor amounts of acid, alcohol and ester is discharged from the reactor into a filter, centrifuge or other liquid/solid separator. Filtration aids optionally are added to increase the ease and speed of the separation. The solids optionally are washed with the alcohol and ester mixture and landfilled or otherwise safely discarded. Recovered solvent is recycled to the Direct Synthesis reactor. An effective amount of a scavenging agent, such as a trialkylorthoester, optionally maybe injected into the recycled solvent to esterify residual traces of acid prior to its reuse. The scavenger also will react with water or any other active hydrogen compounds in the solvent at this point, yielding easily volatilized products. All volatiles are stripped from the solvent as it is being reheated to resume the Direct Synthesis. Silicon and catalyst are added to the hot, stripped solvent with appropriate safety and caution at a temperature below the initiation temperature of the Direct Synthesis.

Alternatively, the hot slurry from the Direct Synthesis optionally is treated with an effective amount of a filtration aid and discharged directly into a solid/liquid separator (for example, centrifuge or filter) for removal of the waste solids. The filtrate, which can still contain ultrafine particulates, is admitted into a separate vessel, or optionally the original reactor, where it is agitated, treated with the carboxylic acid and maintained at a temperature sufficient to volatilize the esters and alcohols. The carboxylic acid is added at a rate and in an amount sufficient to effect removal of silanes, silicates and siloxanes. On completion of the carboxylic acid addition, an orthoester is optionally injected and the additional ester and alcohol are removed. Solids are separated from the remediated solvent, optionally with the assistance of filtration aids, by centrifugation or filtration. The solvent is recycled to the Direct Synthesis.

The following Examples illustrate the preferred embodiments of the instant invention. These are not intended to limit the scope of the invention. Rather, they are presented merely to facilitate the practice of the invention by those of ordinary skill in the art.

EXAMPLES

Abbreviations used in the presentation of the data of the illustrative examples are the following:

TABLE 1

| ABBREVIATION | MEANING |
| --- | --- |
| TMS | HSi(OCH$_3$)$_3$ |
| TTMS | Si(OCH$_3$)$_4$ |
| Selectivity | HSi(OR)$_3$/Si(OR)$_4$ |
| N550BL | NALKYLENE ® 550BL |
| TH 59 | THERMINOL ® 59 |
| sec | second |
| psig | pounds per square inch gauge |
| min | minute |
| hr | hour |
| kPa | kilopascals |

TABLE 1-continued

| ABBREVIATION | MEANING |
|---|---|
| g | gram |
| kg | kilogram |
| L | liters |
| μm | micrometer |
| % Si/hr | percent silicon converted per hour |
| rpm | revolutions per minute |
| $m^2/g$ | square meters per gram |
| wt % | weight percent |
| cm | centimeter |

In the following examples used solvent was analyzed by gravimetry and atomic absorption spectrometry for total silicon content and by $^{29}Si$ NMR for the speciation of the soluble silicon into $Q^0$, $Q^1$, $Q^2$, $Q^3$ and $Q^4$ groups. The chemical shifts (relative to tetramethylsilane) of these functional groups are set forth in Table 2, below. Molar percentages of these groups are calculated from the integration areas.

TABLE 2

| GROUP | STRUCTURE | $^{29}Si$ NMR SHIFTS (ppm) |
|---|---|---|
| $Q^0$ | Si(OR)$_4$ | −78.3 to −78.5 |
| $Q^1$ | O-Si(OR)$_3$ | −85.6 to −85.9 |
| $Q^2$ | O-Si(OR)$_2$-O | −93.6 to −93.9 |
| $Q^3$ | O-Si-O(OR)O | −102.0 to −102.6 |
| $Q^4$ | Si(OSi)$_4$ | −110 |

Preparation of Synthetic Silicate Mixture

Following the procedure published by W. G. Klemperer and S. D. Ramamurthi in "Better Ceramics Through Chemistry III," (Brinkley, Clark and Ulrich, Editors), p.3, a mixture of linear, branched and cyclic silicates was prepared from 112.09 g $CH_3OH$, 22.42 g $HSi(OCH_3)_3$, 86.24 g $Si(OCH_3)_4$, 7.14 g $H_2O$ and 1.45 g 10 molar HCl. This mixture was used in comparative experiments reported in Examples 1–3 to illustrate the spectroscopic properties of alkyl silicates and to illustrate the reactions for $SiOCH_3$ groups with formic and acetic acids.

Example 1

This Example illustrates the content of silicon, dissolved silicate and total solids of waste solvents from laboratory and industrial slurry phase Direct Syntheses of trimethoxysilane.

TABLE 3

Silicon And Silicate Composition of Used Reaction Solvents And Synthetic Silicate Waste

| SAMPLE | wt % Si in SOLVENT | $Q^0$, mole % | $Q^1$, mole % | $Q^2$, mole % | $Q^3$, mole % |
|---|---|---|---|---|---|
| Used TH 59 Laboratory | 0.34 | 0 | 52.3 | 47.7 | 0 |
| Used TH 59 Industrial | 1.85 | 7.9 | 15.5 | 30.6 | 29.5 |
| Used N550 | 0.87 | 0 | 44.2 | 39.8 | 13.8 |
| Synthetic silicate mixture | 9.17 | 13.3 | 34.9 | 35.0 | 12.6 |

Example 2

This Example illustrates that precipitation of silicate solids occurs when solvents which had been used for the Direct Synthesis of trimethoxysilane and triethoxysilane were treated with formic acid or acetic acid. Results are also shown for unused controls and for a comparative sample containing synthesized silicates (vide supra).

Approximately 20 g aliquots of the same used solvents used in example 1 were transferred to small glass vials and shaken with 10 g HCOOH (90 wt %) or 10 g glacial $CH_3COOH$. The samples were left undisturbed at room temperature and observed periodically. Heating was applied in a few cases. The observations are recorded in Table 4.

TABLE 4

Effects of Formic and Acetic Acids on Used Reaction Solvents

| SAMPLE | ACID | OBSERVATIONS |
|---|---|---|
| Used TH 59 Laboratory | HCOOH | Immediately turbid. Crystalline precipitate within 1 hr. Complete precipitation by 24 hr. Solvent less viscous |
| Fresh TH 59 Control | HCOOH | No reaction |
| Fresh TH 59 Control | $CH_3COOH$ | No reaction |
| Used N550 | HCOOH | Immediately turbid. Solid observed after 1 hr. Complete precipitation by 24 hr. Solvent less viscous |
| Fresh N550 Control | HCOOH | No reaction |
| Fresh N550 Control | $CH_3COOH$ | No reaction |
| Synthetic Silicate Mixture | $CH_3COOH$ | Gelation on long standing. Immediate precipitation on heating to 70° C. |
| Synthetic Silicate Mixture | HCOOH | Immediate precipitation |
| Used TH 59 Industrial | HCOOH | Immediate precipitation |
| Used TH 59 Industrial | $CH_3COOH$ | Gelation on long standing |

The experimental results show that precipitation of solids occurred in all used solvent samples which were treated with formic or acetic acid. This precipitation was similar to that observed with a synthetic silicate mixture and provided evidence of the removal of soluble silicates from the used organic solvents Example 3

This Example provides evidence from FTIR and GC/MS analyses that dissolved silicates are removed from the used solvent by treatment with carboxylic acids and that the corresponding alcohols and carboxylic acid esters are formed simultaneously.

THERMINOL®59 which had been used in the commercial Direct Synthesis of $HSi(OCH_3)_3$ was reacted with 90 wt % HCOOH at 50° C. The molar ratios, [HCOOH/Si], used spanned 1.5–6. Reaction was performed in a 250 ml three-necked round bottom flask fitted with a mechanical stirrer, distilling head, water-cooled condenser, thermometer and dropping funnel. The quantities of reagents used are listed in Table 5. The reactions were exothermic to about 60° C. as the formic acid was added to the used THERMINOL®59. Volatile byproducts, precipitated solid and treated solvent were collected for analysis. The reaction mixture was separated by filtration. The filtrate was stripped at 150° C. in vacuo to remove residual methanol, methyl formate and formic acid. The granular solid was rinsed with methanol and dried overnight in an oven at 100° C. The quantity of recovered solid is also recorded in Table 5.

TABLE 5

Quantities of Used Therminol ® 59 and Formic Acid
Employed in Experiments of Example 3

| EXAMPLE | USED TH 59, g | HCOOH, g | [HCOOH/Si], molar ratio | RECOVERED SOLID, g |
|---|---|---|---|---|
| 3A | 50.08 | 10.03 | 5.95 | 2.13 |
| 3B | 50.06 | 8.08 | 4.79 | 2.28 |
| 3C | 50.00 | 5.78 | 3.43 | 2.27 |
| 3D | 50.11 | 3.15 | 1.87 | 2.33 |

FTIR spectra of fresh THERMINOL®59 and used THERMINOL®59 before and after formic acid treatment were measured on thin capillary films between potassium bromide plates. The spectrum of used THERMINOL®59 had significant absorbance in the region, 1020–1150 cm$^{-1}$, characteristic of the Si—O—Si asymmetric stretch. The peak maximum was at 1096.5 cm$^{-1}$. The spectra of fresh and formic acid treated THERMINOL®59 showed no significant absorbance in that region. Additionally, overlays of these two spectra showed them to be identical within experimental error.

The precipitated solids were tan colored. All had FTIR spectra indicating a broad intense band centered at 1072–1075 cm$^{-1}$ suggestive of the Si—O—Si asymmetric stretch of silica and a broad band at 3365 cm$^{-1}$ indicative of hydrogen bonded OH groups. Weak bands at 1276 cm$^{-1}$ and 2955 cm$^{-1}$ indicated CH$_3$ attached to Si. A weak Si—H stretch was observed at 2250 cm$^{-1}$. Water was indicated by a weak band at 1630–1640 cm$^{-1}$.

These FTIR results show that dissolved silicates were present in the used THERMINOL®59 and were responsible for the Si—O—Si band at 1096.5 cm$^{-1}$. Formic acid treatment of the used solvent precipitated the silicates and left a filtrate that was indistinguishable from fresh, unused THERMINOL®59. The precipitated solid contained silica and silsesquioxanes with H$_3$C—Si, H—Si and HO—Si moieties.

Volatile byproducts from the formic acid treatment described above were condensed and analyzed by GC/MS on a Hewlett Packard 5970 instrument. A 30 meter×0.25 mm i.d. DB-5 capillary column with a 0.25 micrometer coating was employed for the separation. Methanol (mass 32) and methyl formate (mass 60) were the principal constituents.

Comparative experiments were performed the synthetic organosilicate mixture prepared hereinabove. The mixture was added to THERMINOL®59 to provide solutions containing 1.25 wt % Si or 2.50 wt % Si. Formic acid was used in amounts corresponding to [HCOOH/Si] molar ratios in the range, 1–4. All reactions were slightly exothermic. Recovered solids, volatile byproducts and treated solvent were analyzed by FTIR and GC/ms as described above. The data showed that dissolved silicon was fully precipitated at [HCOOH/Si] molar ratios >1.

Examples 4–6

These examples illustrate a broad range of temperatures, molar ratios, HCOOH addition rates and reaction times over which the formic acid precipitation step can be performed. Completeness of the reaction and filterability of the solids formed were the two parameters monitored.

Example 4 illustrates the effect of reaction temperatures in the range, 21–90° C., at [HCOOH/Si] molar ratio of about 6. Example 5 illustrates the effect [HCOOH/Si] molar ratios, 0.9–3 and reaction times 1–5 hr. Example 6 illustrates the effect of formic acid addition rates, 0.25–18 g/sec.

Reaction was performed in an appropriately sized three-necked round bottom flask fitted with a mechanical stirrer, distilling head, water-cooled condenser, thermometer and dropping funnel. Formic acid (90 wt %) was added to THERMINOL®59 which had been used in the commercial scale Direct Synthesis of HSi(OCH$_3$)$_3$. In each experiment of Example 4 (Table 6), 500 g used THERMINOL®59 was added to the flask and heated to the set temperature. Formic acid (90 wt %, 100 g) was then introduced at 3 g/sec. Stirring was continued for 1 hr at the set temperature. Filtration was performed through 0.7 micrometer, 142 mm diameter borosilicate microfiber pads in a stainless steel filter pressurized at 20 psi (137.9 kPa) nitrogen. The weight of the filtrate was recorded at 10 second intervals. The solids were rinsed with methanol and dried in an oven at 80° C. to constant weight.

In Example 5 (Table 7), reaction was initiated at 21° C. with 100 g used THERMINOL®59. Formic acid was added at 3 g/sec. Total reaction time was varied from 1–5 hr as shown in Table 8. 300 g used THERMINOL®59, 60 g HCOOH (90 wt %), an initial temperature of 21° C. and total reaction time of 1 hr were the quantities and conditions employed in the study of formic acid addition rate described in Example 6 (Table 8). The reaction mixtures of Examples 5 and 6 were pressure filtered with 20 psig (137.9 kPa) nitrogen through a fine borosilicate membrane 60 mm in diameter. The weight of the filtrate was recorded at 10 second intervals. The solids were rinsed with methanol and dried in an oven at 80° C. to constant weight.

TABLE 6

(Example 4)
Effect of Reaction Temperature on
Silicate Removal and Filterability from
Used Therminol ® 59

| EXAMPLE | TEMPERATURE, ° C. | RECOVERED SOLID, g | FILTRATION RATES, g/sec |
|---|---|---|---|
| 4A | 21 | 40.2 | 11.28 |
| 4B | 35 | 34.0 | 2.06 |
| 4C | 50 | 31.1 | 1.06 |
| 4D | 80 | 32.8 | 11.01 |
| 4E | 90 | 42.8 | 10.79 |

It is apparent from Table 6 that while solids were precipitated at all of the temperatures investigated, filterability appeared to be improved at 21° C. (Example 4A) and 80–90° C. (Examples 4D, 4E) compared to temperatures of 35–50° C.

TABLE 7

(Example 5)
Effect of [HCOOH/Si] Molar Ratio
and Reaction Time at 21° C. on Silicate Removal
and Filterability from Used Therminol ® 59

| EXAMPLE | HCOOH, g | [HCOOH/Si] molar ratio | Reaction Time, hr | Recovered Solids, g | Filtration Rate, g/sec |
|---|---|---|---|---|---|
| 5A | 3.11 | 0.92 | 1 | 6.86 | 0.20 |
| 5B | 3.11 | 0.92 | 2 | 7.02 | not measured |
| 5C | 6.23 | 1.85 | 2 | 7.85 | not measured |
| 5D | 3.11 | 0.92 | 3 | 7.39 | not measured |
| 5E | 6.24 | 1.85 | 1 | 7.80 | 0.56 |
| 5F | 6.23 | 1.85 | 3 | 7.91 | 0.52 |

TABLE 7-continued (Example 5)
Effect of [HCOOH/Si] Molar Ratio
and Reaction Time at 21° C. on Silicate Removal
and Filterability from Used Therminol ® 59

| EX-AMPLE | HCOOH, g | [HCOOH/Si] molar ratio | Reaction Time, hr | Recovered Solids, g | Filtration Rate, g/sec |
|---|---|---|---|---|---|
| 5G | 3.11 | 0.92 | 5 | 7.40 | 0.41 |
| 5H | 9.22 | 2.74 | 1 | 7.92 | 0.88 |
| 5I | 9.24 | 2.74 | 2 | 7.93 | 0.64 |
| 5J | 9.20 | 2.73 | 3 | 7.96 | 0.72 |

The data of Table 7 show that the solids formed in Examples 5E, 5F, 5H, 5I and 5J were more readily filterable than those in Examples 5A and 5G. Thus, it appears that [HCOOH/Si] molar ratios 1.5–3 and reaction times of about 1 hour are highly desirable conditions for the removal of dissolved silicates from the used reaction solvent.

TABLE 8

(Example 6)
Effect of HCOOH Addtion Rate at
21° C. on Solids Filterability

| EXAMPLE | HCOOH, g/sec | FILTRATION RATE, g/sec |
|---|---|---|
| 6A | 0.25 | 0.92 |
| 6B | 2.80 | 0.88 |
| 6C | 17.91 | 0.59 |

It is clear from Table 8 that slower addition of formic acid yielded solids that were more easily filtered.

Example 7

This Example illustrates the removal of residual formic acid from used THERMINOL®59 following precipitation of dissolved silicates. Both scavenging of residual formic acid with trimethylorthoformate and evaporative removal of the residual acid are illustrated.

302.5 g THERMINOL®59 which had been used in the commercial Direct Synthesis of $HSi(OCH_3)_3$ was reacted with 50.2 g 90 wt % HCOOH at 50° C. for 1 hr. The molar ratio, [HCOOH/Si], was 4.92. Reaction was performed in a 500 ml three-necked round bottom flask fitted with a mechanical stirrer, distilling head, water-cooled condenser, thermometer and dropping funnel. The reaction mixture was pressure filtered with 20 psig (137.9 kPa) nitrogen through a fine borosilicate membrane 60 mm in diameter. The filtrate (Sample 7A in Table 9) was divided into two portions for removal of residual formic acid. One portion of about 100 g was heated to 150° C. for 1 hr and stripped of its volatiles in a stream of flowing nitrogen. The recovered solvent is labeled Sample 7B in Table 9. Another portion (150 g) of the filtrate was reacted with 5.82 g $HC(OCH_3)_3$ at 21° C. and then heated to 70° C. in flowing nitrogen to strip the contained volatiles. Solvent recovered from this treatment is labeled Sample 7C in Table 9. All three samples were analyzed by FTIR as capillary films between KBr plates.

TABLE 9

FTIR Results For Recovered Therminol ® 59
Treated to Remove Residual Formic Acid

| SAMPLE | FTIR RESULTS |
|---|---|
| Fresh THERMINOL ® 59 | No Si-O-Si or C=O bands |
| Used THERMINOL ® 59 | Si-O-Si bands at 1096.5 $cm^{-1}$. No C=O band |
| 7A | No Si-O-Si band. Small C=O band at 1731 $cm^{-1}$ with lower frequency shoulder |
| 7B | No Si-O-Si or C=O bands |
| 7C | No Si-O-Si or C=O bands |

The results summarized in Table 9 show that the FTIR spectra of Samples 7B, 7C and fresh THERMINOL®59 were indistinguishable. All three contained no dissolved silicate or carbonyl-containing compounds such as formic acid or methyl formate. Both formic acid and methyl formate were present in the initially treated THERMINOL®59, Sample 7A. The carbonyl band was a superposition of an ester carbonyl (methyl formate) and an acid carbonyl (formic acid), the latter indicated by the low frequency shoulder. Thus, both the $HC(OCH_3)_3$ scavenging and the evaporative separation removed residual formic acid from THERMINOL®59 following precipitation of dissolved silicates.

Example 8

This Example illustrates the improvements in solid/liquid separation rate effected by the addition of filter aids to the used reaction solvent. Several polyacrylate (GOOD-RITE®7058, CARBOPOL®980, PEMULEN®, cellulose-based (SOLKAFLOC®), sorbitol-based (MILLITHIX®925) and polyethylene oxide filtration aids were tested. The data shown in Table 10 are for 0.5 wt % used level in used THERMINOL®59 from the commercial scale Direct Synthesis of $HSi(OCH_3)_3$ In each experiment, 200 g of the sued solvent were stirred at 21° C. with the appropriate filter aid. Filtration was performed through 142 mm diameter, 0.7 micrometer borosilicate microfiber pads in a stainless steel filter pressurized at 20 psi 137.9 kPa) nitrogen. Filtrate was weighed continuously during collection and a plot of weight versus time was constructed. The rate (g/min) shown in Table 10 is the slope of the linear, rising portion of the curve. Approximately 190 g was recovered from each experiment.

TABLE 10

Filtration of Used Therminol ® 59 with Filtration Aids.

| FILTER AID | WEIGHT OF FILTRATE, g | TOTAL TIME, min | FILTRATION RATE, g/min |
|---|---|---|---|
| None | 192.0 | 15.5 | 22.31 |
| GOOD-RITE ® 7058 | 189.4 | 4.67 | 130.95 |
| CARBOPOL ® 980 | 189.5 | 9.67 | 43.64 |
| MILLITHIX ® 925 | 191.7 | 10.83 | 26.22 |
| POLYOX 7 × $10^6$ daltons | 191.8 | 9.50 | 34.53 |
| PEMULEN ® TR1 | 192.0 | 8.00 | 48.94 |
| PEMULEN ® TR2 | 192.0 | 8.50 | 48.92 |
| PEMULEN ® 1622 | 191.0 | 8.17 | 48.84 |
| SOLKAFLOC ® | 192.0 | 4.67 | 121.43 |

The data of Table 10 show that filtration was enhanced to difference extents with the addition of 0.5 wt % filter aid.

Polyacrylate and cellulose-based materials afforded rate improvements 2–6 times the control value. GOOD-RITE®7058 and SOLKAFLOC® were especially effective.

Example 9

This Example illustrates the use of formic acid and trimethylorthoformate in the remediation of unfiltered THERMINOL®59 from the Direct Synthesis of trimethoxysilane.

THERMINOL®59 which had been recycled four times to the Direct Synthesis of $HSi(OCH_3)_3$ without removal of the dissolved silicates was the starting material. It contained 1.85 wt % dissolved silicon, 2.95 wt % total silicon and 4.03 wt % solids. 3.33 kg of this unfiltered waste was charged to a 5 L four neck flask (fitted with mechanical agitator, distilling head, thermometer, condenser and nitrogen sparger) and reacted at room temperature (21° C.) with 208 g HCOOH (90 wt %), which was added at 10.5 g/min. The molar ratio, [HCOOH/Si], was 1.85. Stirring was continued for a total of 1 hr prior to pressure filtration of the solids through a 0.7 micrometer, 142 mm diameter borosilicate pad at 20 psi (137.9 kPa). The filtrate still contained methanol, methyl formate and a slight excess of formic acid. It was treated with 21.26 g $HC(OCH_3)_3$ to scavenge the unreacted HCOOH and the whole stripped of volatiles by heating to 100° C. in flowing nitrogen for about 1 hr. The recovered solvent was used to prepare trimethoxysilane (See Example 12E).

Example 10

This Example illustrates the filtration and formic acid treatment of used THERMINOL®59 from the Direct synthesis of trimethoxysilane.

THERMINOL®59 which had been recycled four times to the Direct Synthesis of $HSi(OCH_3)_3$ without removal of the dissolved silicates was the starting material. It contained 1.85 wt % dissolved silicon, 2.95 wt % total silicon and 4.03 wt % solids. SOLKAFLOC® filter aid was added to the used solvent and the resulting slurry was pressure filtered at 40 psig (275.8 kPa) through a 0.7 micrometer, 142 mm diameter borosilicate pad. 2580.6 g filtered waste was then treated with 150.22 g HCOOH (90 wt %) at room temperature for 2.5 hr. The molar ratio, [HCOOH/Si], was 1.73. Pressure filtration through a 0.7 micrometer, 142 mm diameter borosilicate pad produced 108.2 g silicate solids and a filtrate comprising THERMINOL®59, methanol, methyl formate and, possibly, formic acid. The filtrate was stripped of volatiles in flowing nitrogen by heating it to 150° C. and maintaining that temperature for 1 hr. 2424.6 g of remediated THERMINOL®59 was recovered for reuse in the Direct Synthesis (See Example 12D).

Example 11

Comparative Example

Therminol®59 Treatment with Boric Acid/Sodium Methoxide

This comparative Example is used to obtain a sample of remediated THERMINOL®59 using the method disclosed in U.S. Pat. No. 5,166,384 (Example 21).

THERMINOL®59 which had been recycled four times to the Direct Synthesis of $HSi(OCH_3)_3$ without removal of the dissolved silicates was the starting material. It contained 1.85 wt % dissolved silicon, 2.95 wt % total silicon and 4.03 wt % solids. 2.85 kg of this unfiltered waste was charged to a 4 L four neck flask (fitted with mechanical agitator, distilling head, thermometer, condenser and nitrogen sparger), stirred and heated to 65° C. 12.25 g $NaOCH_3$ powder was added followed, one minute later, by 37.1 g $H_3BO_3$. The temperature was increased to 85° C. and maintained there for 2 hr. The hot reaction mixture was then pressure filtered through a 0.7 micrometer, 142 mm diameter borosilicate pad at 20 psi (137.9 kPa). Recovered filtrate was used for the Direct Synthesis of trimethoxysilane in Example 12C.

Example 12

This Example illustrates the reuse of the THERMINOL®59 solvent recovered as described hereinabove in Examples 9–11 in the slurry phase Direct Synthesis of $HSi(OCH_3)_3$.

Equipment Used

A 5.8 liter CHEMINEER® reactor was used for Direct Reactions of silicon and methanol in Examples 12A–12E. Four 90° spaced, 1.27 cm wide baffles were affixed to the wall of the reactor. Agitation was provided by two stirrers attached to an axial shaft. The bottom one was a six blade turbine, 6.35 cm in diameter. A four blade propeller of the same diameter was placed 10 cm above the turbine. Power for agitation was provided by a variable speed air-driven motor whose rotation speed was measured by a magnetic tachometer. An electric heating mantle controlled by a heater/temperature controller was used to heat the reactor.

Methanol was supplied to the reactor from a 1 L storage container via a calibrated FMI laboratory pump. Coiled stainless steel tubing, 0.32 cm internal diameter×305 cm length, placed in a 4 L silicone oil bath controlled at 150° C. served as the alcohol vaporizer. A similar vaporizer coil was available for the recycle stream, but it was not used during the course of these experiments. The alcohol inlet line entered through the top of the reactor. It was heat traced to prevent condensation of the vapor. Alcohol vapor was injected 2.5 cm from the bottom of the reactor and below the level of the six-blade turbine through a single downward pointing (0.63 cm internal diameter) sparger. A pressure gauge attached the alcohol vapor inlet line gave higher readings (up to about 2 atmospheres) when the sparger was plugged. Ordinarily, the gauge was at zero. Additional alcohol was supplied to the storage container during an experiment to maintain an uninterrupted flow of this reagent.

Reaction products and unreacted alcohol exited the reactor through a 91.4 cm×2.54 cm internal diameter packed tube, which served as entrainment separator and partial distillation column to remove solvent and higher boiling silicates from the product stream. The packing was ceramic saddles and stainless steel mesh. Five thermocouples were distributed along the length of the tube to record temperatures and indicate foaming. The lowest thermocouple was flush with the top of the reactor. Foaming was controlled by the use of FS 1265. Flexible tubing connected the outlet of the entrainment separator/partial distillation column to the four-way valve.

Two ten plate Oldershaw distillation columns served to separate the liquid reaction products and unreacted alcohol from the gases. Effluent from the reactor was admitted into the top trays of the lower column, which was attached to a 3 neck 2 L round bottom flask supported in a heating mantle. The upper column was capped by a magnetically controlled reflux condenser and distillation head with thermocouple. The reflux condenser and another condenser downstream were cooled to –25° C. by circulating silicone oil. Uncondensed gases exited the condenser through a vapor lock bubbler into the total gas flow meter (Model DTM-115, American Meter Co.). Wider tubing was employed downstream of the bubbler to avoid backpressures likely to shatter the glassware (columns, condensers and bubbler) or cause leaks at the joints. A gas sampling port was provided at a T joint following the gas meter. Gas flow from the meter was diluted with nitrogen prior to its discharge into the laboratory hood. A thermocouple was located in the second opening of the three neck flask and the intake to an FMI laboratory pump in the other. The pump was used to transfer liquid product from the flask to TEFLON® coated polyethylene storage bottles. All glass containers used to store or sample trimethoxysilane were washed with dilute HCl, rinsed thoroughly with methanol and oven dried at 110° C. prior to use.

General Activation and Reaction Procedure

In all cases, the reactor was charged with 2 kg solvent, 1 kg silicon, 7.05 g copper (II) hydroxide catalyst and 0.6 g FS-1265 defoamer and sealed. According to equation [1], complete conversion of 1 kg silicon will require 3.43 kg methanol and produce 4.36 kg $HSi(OCH_3)_3$ and 873 L $H_2$ at 298 K and 1 atmosphere. The slurry was agitated at about 900–1200 rpm and nitrogen introduced as it was heated to 250° C. Simultaneous with the silicon-catalyst thermal activation, the alcohol vaporizer was heated to about 150° C. and the refrigerant circulating through the condenser was cooled to about 25° C. Alcohol flow to the reactor was initiated after the slurry had been at 250° C. for one hour. The flow rate was 5.05 g/min.

Once the alcohol flow was underway, sampling and analysis of the vent gas stream for hydrogen were done every 10 minutes until a stable composition was established. That indicated the end of the induction period. Thereafter, gas sampling was done every 30 minutes to monitor hydrogen, hydrocarbons and ethers. During the course of the reaction, total vent gas flow was used as an approximate measure of the reaction rate according to the stoichiometry of equation [1].

Samples were collected in previously acid washed, methanol rinsed, oven dried containers attached at the four-way sampling valve for 2–5 minutes every half hour. The containers were cooled in dry-ice during sample collection. Samples were weighed and analyzed by gas chromatography. The bulk of the liquid product was condensed in the three neck flask, which served as the reboiler, and transferred to storage. All of these data were used to calculate the temporal composition of the product stream, its selectivity to trialkoxysilane, the reaction rate and overall silicon conversion. Usually, reactions were terminated after >85% of the silicon charged to the reactor had been reacted.

Gas samples were analyzed for hydrogen, nitrogen and methane content on a Hewlett Packard 5840 gas chromatograph fitted with a GS-Molesieve 30 m×0.53 mm internal diameter (J & W Scientific) capillary column and flame ionization detector. Argon was the carrier gas. Gas chromatography-mass spectrometry was used to analyze for dimethyl ether. Liquid samples containing alkoxysilanes were analyzed on a Hewlett Packard 5890 gas chromatograph fitted with a 3.66 m×3.18 mm internal diameter stainless steel 20% OV-101 on 60/80 mesh CHROMOSORB WHP column (Supelco) and thermal conductivity detector. Helium was the carrier gas.

Materials Used

Analytical and particle size data for the technical grade silicon utilized in the experiments of the illustrative Examples 12A–12E are listed in Tables 11 and 12. Table 13 presents a data summary for the copper (II) hydroxide catalyst used. NALKYLENE®550 BL and THERMINOL®59 were the solvents used. FS 1265 (Dow Corning) was the foam control agent.

TABLE 11

Composition of Silicon Sample Used in Examples 12A–12E

| ELEMENT | VALUE |
|---|---|
| Al, wt % | 0.08 |
| Ba, ppm | <3 |
| Ca, ppm | 600 |
| Cr, ppm | 58.9 |
| Cu, ppm | 34.8 |
| Fe, wt % | 0.38 |
| Mg, ppm | 8.8 |
| Mn, ppm | 90.4 |
| Ni, ppm | 15.5 |
| P, ppm | 26.8 |
| Pb, ppm | <10 |
| Sn, ppm | <10 |
| Ti, ppm | 299 |
| V, ppm | 14.3 |
| Zn, ppm | <5 |
| Zr, ppm | 29 |

TABLE 12

Particle Size Distribution of Silicon Samples Used in Examples 12A–12E

| NOMINAL SIEVE SIZE, μm | Wt % > NOMINAL SIZE |
|---|---|
| 600 | 3.1 |
| 425 | 14.0 |
| 300 | 18.7 |
| 250 | 13.7 |
| 180 | 11.9 |
| 75 | 24.1 |
| 45 | 1.5 |
| <45 | 11.6 |

TABLE 13

Characterization of Copper (II) Hydroxide Catalysts Used in Illustrative Examples

| PROPERTY | VALUE |
|---|---|
| Cu, wt % | 58.12 |
| Al, ppm | 2580 |
| As, ppm | <30 |
| Ca, ppm | 1530 |
| Fe, ppm | 610 |
| P, wt % | 1.62 |
| Pb, ppm | 290 |
| Sb, ppm | 20 |
| Sn, ppm | 80 |
| Zn, ppm | 950 |
| $H_2O$, wt % | 6.0 |
| $Cl^-$, ppm | 310 |
| $SO_4^{2-}$, wt % | 1.72 |

The Direct Synthesis was performed in the 5.8 L CHEMINEER® reactor as described hereinabove. Example 12A is a control experiment with fresh THERMINOL®59. Example 12B was conducted with used THERMINOL®59 (same starting material from Examples 9–11) which had been pressure filtered to remove suspended solids, but which was untreated otherwise. The solvent for Example 12C was that recovered in Example 11 according to the method of U.S. Pat. No. 5,166,384. THERMINOL®59 used in Examples 12D and 12E was obtained with formic acid remediation as disclosed in Examples 10 and 9, respectively.

Table 14 contains a summary of the performance parameters for the five experiments at 85% silicon conversion.

Reactions were actually continued beyond this point, but 85% is a convenient criterion for comparison.

TABLE 14

Direct Synthesis of HSi(OCH$_3$)$_3$ with Remediated Therminol ® 59

| EXAMPLE | Si Conv. (%) | Rate, (% Si/hr) | HSi(OCH$_3$)$_3$ (kg) | Si(OCH$_3$)$_4$ (kg) | Selectivity* |
|---|---|---|---|---|---|
| 12A Control with fresh TH 59 | 85 | 6.72 | 3.53 | 0.148 | 23.94 |
| 12B Filtered, used TH 59 | 85 | 5.95 | 3.54 | 0.140 | 25.36 |
| 12C TH 59 from Ex. 11 | 85 | 6.25 | 3.51 | 0.152 | 23.17 |
| 12D TH 59 from Ex. 10 | 85 | 6.15 | 3.55 | 0.121 | 29.40 |
| 12E TH 59 from Ex. 9 | 85 | 6.44 | 3.60 | 0.112 | 32.07 |

*Selectivity is the gravimetric ratio, HSi(OCH$_3$)$_3$/Si(OCH$_3$)$_4$

The filtered THERMINOL®59 of Example 12B was visibly more viscous than the fresh THERMINOL®59 of Example 12A, or the remediated solvents of Examples 12C, 12D and 12E. The slower silicon conversion rate in Example 12B might reflect the higher resistance to methanol mass transfer in this more viscous medium and illustrates the need for solvent remediation after a number of cycles of reuse. Selectivities in Examples 12A, 12B and 12C were very good and comparable to values disclosed in U.S. Pat. Nos. 4,727,173 and 5,166,384. reaction rates and selectivities were excellent with the remediated solvents (Examples 12D and 12E) of the instant invention.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A process for remediating a used solvent containing dissolved silicon compounds therein, the process comprising:
   contacting the used solvent with a sufficient amount of a carboxylic acid so as to effect a reaction which converts said dissolved silicon compounds to solid silicates and/or silica; and then,
   separating the solvent from the solid silicates and/or silica.

2. A process as in claim 1 wherein, prior to said contacting step the solvent is separated from solids suspended therein.

3. A process as in claim 2 wherein carboxylic acid is added to the used solvent in an amount which provides a ratio of carboxylic acid equivalents per silicon atom (COOH/Si) of from 0.5 to 6.

4. A process as in claim 3 wherein the ratio COOH/Si is 1–3.

5. A process as in claim 1 wherein an excess of acid is used and, after said solid silicates and/or silica are produced, excess acid is stripped from the solvent.

6. A process as in claim 1 wherein after said solid silicates and/or silica are produced, a scavenger is added to the solvent to react with any residual active hydrogen before it is reused.

7. A process as in claim 6 wherein the scavenger is a trialkylorthoester.

8. A process as in claim 6 wherein the scavenger is selected from the group consisting of HC(OCH$_3$)$_3$, HC(OC$_2$H$_5$)$_3$, CH$_3$C(OC$_2$H$_5$)$_3$, CH$_3$C(OC$_3$H$_7$)$_2$OC$_2$H$_5$, C(OCH$_3$)$_4$, C(OC$_2$H$_5$)$_4$ and C(OC$_3$H$_7$)$_4$.

9. A process as in claim 1 wherein the concentration of the carboxylic acid is at least 10% by weight.

10. A process as in claim 9 wherein the concentration of the carboxylic acid is at least 25% by weight.

11. A process as in claim 1 wherein said reaction is effected at a temperature of 15–250° C.

12. A process as in claim 11 wherein said reaction is effected at a temperature of 20–100° C.

13. A process as in claim 1 wherein the carboxylic acid is acetic or formic acid.

14. A process as in claim 13 wherein the concentration of the acetic acid or formic acid used is at least 80% by weight.

15. A process as in claim 1 wherein the carboxylic acid is selected from the group consisting of formic, acetic, furoic, acetoacetic, chloroacetic, chloropropanoic, trichloroacetic, bromoacetic, fluoroacetic, trifluoroacetic, bromobenzoic, chlorobenzoic, lactic, glycolic, salicylic, oxalic, maleic, fumaric, itaconic, succinic, adipic, citric, tartaric and polyacrylic acids and mixtures thereof.

16. A process as in claim 1 wherein said reaction is effected at a temperature above the higher of the normal boiling points of said alcohol and of the ester of said alcohol and said acid.

17. A process as in claim 1 wherein the reaction solvent has a boiling point of greater than 250° C.

18. A process as in claim 17 wherein the reaction solvent is an alkylated aromatic compound, a polyaromatic compound, triethyleneglycol dimethyl ether or a mixture of two or more thereof.

19. A process as in claim 17 wherein the reaction solvent comprises at least one member selected from the group consisting of diphenyl ether, diphenyl, terphenyl, alkylated benzenes, alkylated diphenyls, alkylated terphenyls, dibenzyl benzenes, benzyl toluenes, hydrogenated terphenyls and triethylene glycol dimethyl ether.

20. A process as in claim 1 further comprising adding a filtration aid prior to or subsequent to contacting the used solvent with the carboxylic acid.

21. A process as in claim 20 wherein said filtration aid is a member of the group consisting of cellulosic, acrylic, polyethylene oxide, polypropylene oxide, poly(ethylene oxide/propylene oxide) copolymers, diatomaceous and inorganic silicate filter aids, and mixtures thereof.

22. A process as in claim 1 wherein the solvent is a used solvent from a Direct Synthesis process for production of an alkoxysilane.

23. A process as in claim 22 wherein the alkoxysilane is a trialkoxysilane or a tetraalkoxysilane.

24. A process comprising:
   a) reacting a mixture of silicon and alcohol in a reaction solvent under conditions which produce an alkoxysilane product;
   b) separating the alkoxysilane product from the reaction mixture; and then,
   c) remediating the used solvent by
      i) contacting the used solvent with a sufficient amount of a carboxylic acid so as to effect a reaction which converts dissolved silicon compounds in the used solvents to solid silicates and/or silica; and then,
      ii) separating the solvent from the solid silicates and/or silica.

* * * * *